(12) United States Patent
Corrao et al.

(10) Patent No.: US 8,147,531 B2
(45) Date of Patent: Apr. 3, 2012

(54) COMPRESSION PIN WITH OPPOSED THREADED REGIONS

(75) Inventors: Ernie Corrao, Bethel, CT (US); Rebecca Hawkins Wahl, Escondido, CA (US); Alan G. Taylor, Memphis, TN (US)

(73) Assignee: Tornier, Inc., Edina, MN (US)

( * ) Notice: Subject to any disclaimer, the term of this patent is extended or adjusted under 35 U.S.C. 154(b) by 680 days.

(21) Appl. No.: 11/724,415

(22) Filed: Mar. 15, 2007

(65) Prior Publication Data

US 2007/0233124 A1  Oct. 4, 2007

Related U.S. Application Data

(60) Provisional application No. 60/783,760, filed on Mar. 17, 2006.

(51) Int. Cl.
*A61B 17/86* (2006.01)
*A61F 2/08* (2006.01)

(52) U.S. Cl. ........ 606/301; 606/315; 606/316; 606/317; 411/244; 411/378; 411/412; 411/413

(58) Field of Classification Search .......... 606/300–321; 411/378–426
See application file for complete search history.

(56) References Cited

U.S. PATENT DOCUMENTS

| | | | | |
|---|---|---|---|---|
| 4,059,102 A | * | 11/1977 | Devas | 606/309 |
| 5,019,079 A | * | 5/1991 | Ross | 606/312 |
| 5,403,136 A | * | 4/1995 | Mathys | 411/310 |
| 5,544,993 A | * | 8/1996 | Harle | 411/414 |
| 5,593,410 A | * | 1/1997 | Vrespa | 606/312 |
| 5,964,768 A | * | 10/1999 | Huebner | 606/317 |
| 6,030,162 A | * | 2/2000 | Huebner | 411/413 |
| 6,299,615 B1 | * | 10/2001 | Huebner | 606/317 |
| 6,468,277 B1 | * | 10/2002 | Justin et al. | 606/65 |
| 6,585,740 B2 | * | 7/2003 | Schlapfer et al. | 606/308 |
| 6,811,552 B2 | * | 11/2004 | Weil et al. | 606/311 |
| 6,887,242 B2 | * | 5/2005 | Doubler et al. | 606/274 |
| 6,949,100 B1 | * | 9/2005 | Venturini | 606/318 |
| 6,984,235 B2 | * | 1/2006 | Huebner | 470/10 |

(Continued)

FOREIGN PATENT DOCUMENTS

EP  1 297 793 A1  4/2003

(Continued)

OTHER PUBLICATIONS

Search Report and Written Opinion for PCT/US2007/06632, Feb. 20, 2008, Ernie Corrao et al.

(Continued)

*Primary Examiner* — Thomas C. Barrett
*Assistant Examiner* — Matthew Lawson
(74) *Attorney, Agent, or Firm* — Faegre Baker Daniels LLP

(57) ABSTRACT

A compression pin for urging two bone regions together includes a pin body having a distal end, an opposed proximal end, a first threaded region, and a second threaded region. The first threaded region is positioned near the distal end, and the second threaded region is positioned near the first threaded region. The first threaded region includes a first thread having a FT leading surface that is at a FT leading angle, and the second threaded region includes a second thread having a ST leading surface that is at a ST leading angle that is different than the FT leading angle. During insertion of the compression pin, the first threaded region and the second threaded region cooperate to aggressively compress the bone regions together.

22 Claims, 8 Drawing Sheets

U.S. PATENT DOCUMENTS

| | | | |
|---|---|---|---|
| 6,989,014 B2 * | 1/2006 | Justin et al. | 606/316 |
| 7,578,836 B2 * | 8/2009 | Justin et al. | 606/291 |
| 2001/0037113 A1 * | 11/2001 | Justin | 606/73 |
| 2002/0183751 A1 * | 12/2002 | Justin et al. | 606/65 |
| 2003/0014054 A1 * | 1/2003 | Huebner | 606/73 |
| 2003/0045881 A1 * | 3/2003 | Barouk et al. | 606/73 |
| 2004/0006346 A1 * | 1/2004 | Holmen et al. | 606/73 |
| 2004/0210227 A1 * | 10/2004 | Trail et al. | 606/73 |
| 2005/0038438 A1 * | 2/2005 | Anderson et al. | 606/73 |
| 2006/0106390 A1 * | 5/2006 | Jensen et al. | 606/73 |
| 2006/0149265 A1 * | 7/2006 | James et al. | 606/73 |
| 2006/0229622 A1 * | 10/2006 | Huebner et al. | 606/73 |
| 2008/0015595 A1 * | 1/2008 | Renard et al. | 606/73 |

FOREIGN PATENT DOCUMENTS

| | | |
|---|---|---|
| EP | 1297793 A1 | 4/2003 |
| EP | 1 273 272 B8 | 10/2005 |
| EP | 1273272 B8 | 10/2005 |
| FR | 2808182 | 11/2001 |

OTHER PUBLICATIONS

Brochure for T.A.C'. pin, threaded compression pin.
International Preliminary Report on Patentability and Written Opinion for PCT/US2007/006632, publication date Oct. 2, 2008, Nexa Orthopedics, Inc. (now assigned to Tornier, Inc. on Feb. 29, 2008).

* cited by examiner

US 8,147,531 B2

COMPRESSION PIN WITH OPPOSED THREADED REGIONS

RELATED APPLICATION

This Application claims priority on U.S. Provisional Patent Application Ser. No. 60/783,760 filed on Mar. 17, 2006 and entitled "COMPRESSION PIN WITH OPPOSED THREADED REGIONS". The contents of U.S. Provisional Application Ser. No. 60/783,760 are incorporated herein by reference.

BACKGROUND

It is often necessary to fuse two bone regions to repair a fracture or to fuse a joint. On type of device used to fuse two bone regions is a compression pin that utilizes a generally cylindrical shaped pin that is threaded. With this device, the compression pin is threaded into the bone regions and pulls the bone regions together. Unfortunately, in certain instances, existing compression pins do not adequately pull the two bone regions together. As a result thereof, the fusing of the bone regions can be compromised.

SUMMARY

The present invention is directed toward a compression pin for urging two bone regions together. The compression pin includes a pin body having a distal end, an opposed proximal end, a first threaded region, and a second threaded region. The first threaded region is positioned near the distal end, and the second threaded region positioned near the first threaded region. The first threaded region includes a first thread having a FT leading surface that is at a FT leading angle, and the second threaded region includes a second thread having a ST leading surface that is at a ST leading angle. In one embodiment, the FT leading angle is different than the ST leading angle. For example, the FT leading angle can be approximately thirty degrees and the ST leading angle can be approximately two degrees.

With this design, in certain embodiments, during insertion of the compression pin, the first threaded region and the second threaded region cooperate to aggressively compress the bone regions together.

Additionally, the first thread can include a FT trailing surface that is at a FT trailing angle, and the second thread can include a ST trailing surface that is at a ST trailing angle. In one embodiment, the FT trailing angle is different than the ST trailing angle. For example, the FT trailing angle can be approximately two degrees and the ST trailing angle can be approximately thirty degrees.

Moreover, the first thread can have a FT root width, and the second thread can have a ST root width. In one embodiment, the FT root width is different than the ST root width. For example, the FT root width can be approximately 1.5 times greater than the ST root width.

Further, the first thread has a first thread shape and the second thread has a second thread shape. In one embodiment, the first thread shape is substantially opposite to the second thread shape. Stated in another fashion, in certain embodiments, the first thread shape is an approximate mirror image to the second thread shape. With this design, during insertion of the compression pin, the threaded regions cooperate to aggressively compress the bone regions together.

The present invention is also directed to a method for manufacturing a compression pin.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
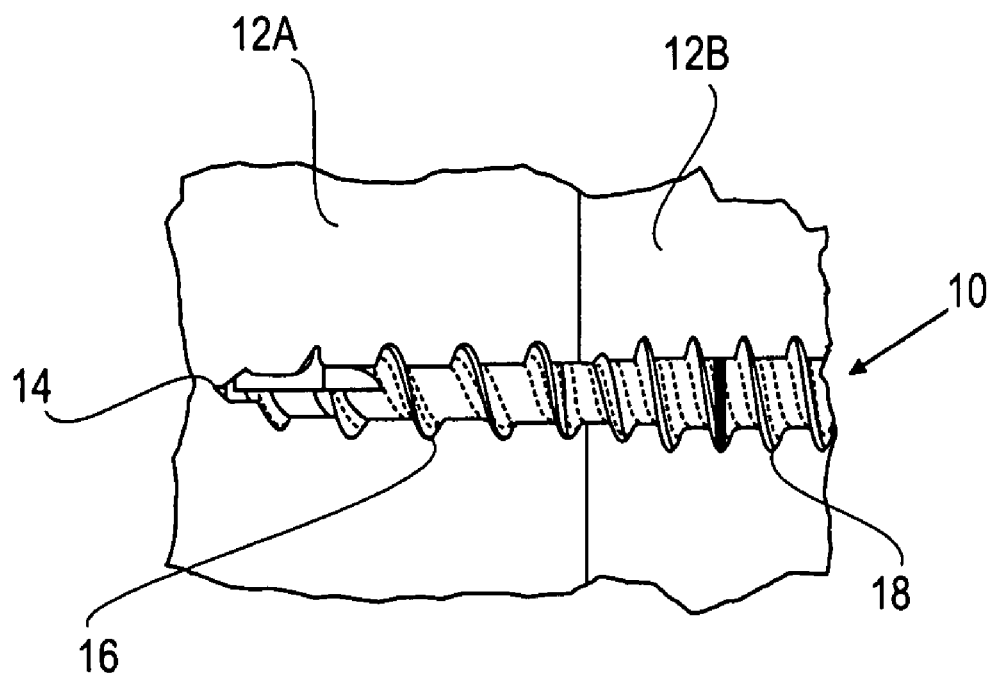
FIG. 1 is a simplified side illustration of a pair of bone regions, in cut-away, that are fused together with a compression pin having features of the present invention.

FIG. 1 is a simplified side illustration a portion of a compression pin 10 having features of the present invention, a first bone region 12A and a second bone region 12B. In this embodiment, the compression pin 10 urges the bone regions 12A, 12B together so that the bone regions 12A, 12B are fused together. The type and location of the bone regions 12A, 12B urged together can vary. For example, the compression pin 10 can be used to fuse a fracture of a human bone, to immobilize and fuse a human joint, or to fuse together adjacent bones.

The compression pin 10 includes a pin body 14 having an externally threaded, first threaded region 16, and an externally threaded, second threaded region 18. In one embodiment, during insertion of the compression pin 10, the first threaded region 16 is initially threaded through the second bone region 12B into the first bone region 12A. Further, as the first threaded region 16 is threaded into the first bone region 12A, the second threaded region 18 is threaded into the second bone region 12B.

It should be noted that in certain embodiments, the first threaded region 16 and the second threaded region 18 are uniquely designed so that the bone regions 12A, 12B are aggressively compressed together during insertion of the compression pin 10. Stated in another fashion, with the design of the threaded regions 16, 18, during insertion of the compression pin 10, the bone regions 12A, 12B are urged together with relatively high forces. As a result thereof, the bone regions 12A, 12B are securely fused together and the likelihood of success of the fusion is enhanced.

In one embodiment, the compression pin 10 is rotated by a wire driver (not shown) to insert the compression pin 10 into the bone regions 12A, 12B. Alternatively, for example, the compression pin 10 can be manually rotated by a screwdriver type device.

In FIG. 1, a portion of the compression pin 10 that extends past the second bone region 12B has been cut-off, e.g. with a pin cutter, after insertion of the compression pin 10.

It should be noted that the compression pin 10 can be inserted with a pilot hole (not shown) or without a pilot hole, depending upon the condition and type of bone regions 12A, 12B.

Figure 2A:
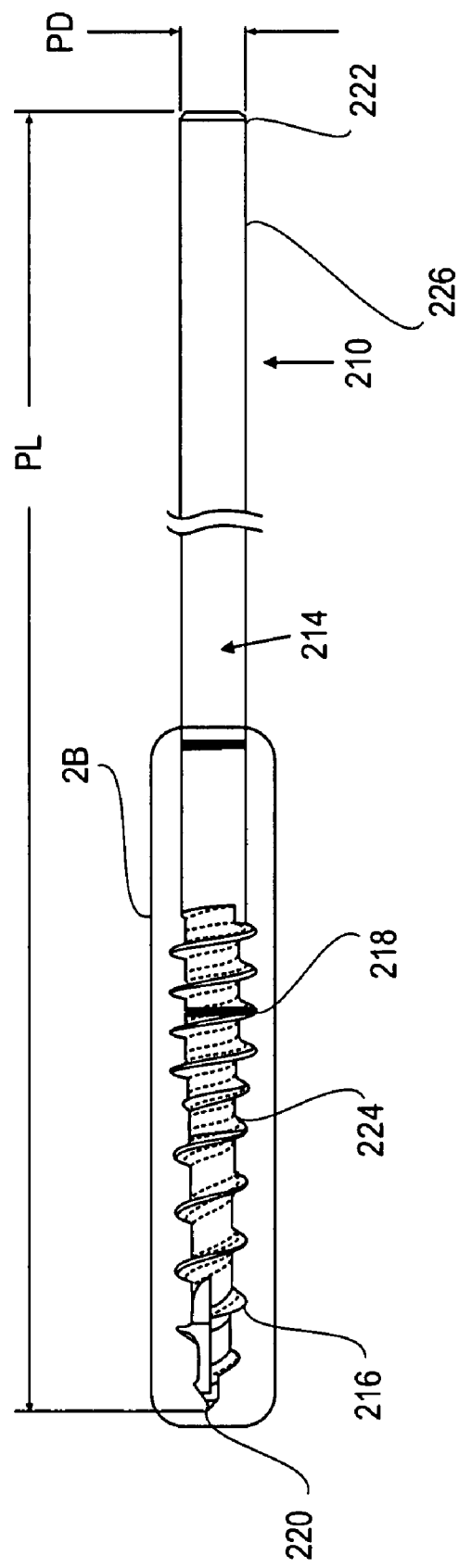
FIG. 2A is a side view of a first embodiment of a compression pin having features of the present invention.

FIG. 2A is a side view of a first embodiment of a compression pin 210. The size, shape, and design of the compression pin 210 can vary according to the teachings provided herein to meet the design requirements of the compression pin 210. In the embodiment illustrated in FIG. 2A, the pin body 214 is generally circular cylinder shaped and has a generally circular shaped cross-section. In alternative, non-exclusive embodiments, the pin body 214 has a pin diameter (PD) of approximately 0.05, 0.06, 0.07, 0.08, 0.09, or 0.1 inches. Further, in alternative, non-exclusive embodiments, the pin body 214 has a pin length (PL) of approximately 2.5, 3.1, 3.4, 4.5, 3.6, or 3.7 inches. However, greater or lesser diameters and lengths can be utilized. In FIG. 2A, the pin lengths PL is approximately 3.15 inches and the pin diameter PD is approximately 0.062 inches. Alternatively, the pin body 214 can have other geometries.

Further, in this embodiment, the pin body 214 includes a distal end 220, a proximal end 222, the first threaded region 216 positioned near the distal end 220, the second threaded region 218 positioned near the first threaded region 216, a transition region 224 positioned between the threaded regions 216, 218, and a driver region 226 positioned near the proximal end 222. The driver region 226 is designed to be engaged by the wire driver for insertion of the compression pin 210. Further, the driver region 226 can be cut off after the compression pin 210 has been inserted into the bone regions 12A, 12B (illustrated in FIG. 1). The proximal end 222 can be tapered for ease of insertion into the wire driver.

In one embodiment, the compression pin 210 is integrally formed as a unitary structure. Alternatively, portions of the compression pin 210 can separately formed and joined together during manufacturing. The type of material utilized in the pin body 214 can be varied to meet the bone regions being fused. For example, the pin body 214 can be formed titanium, stainless steel, or a bio-absorbable material.

Figure 2B:
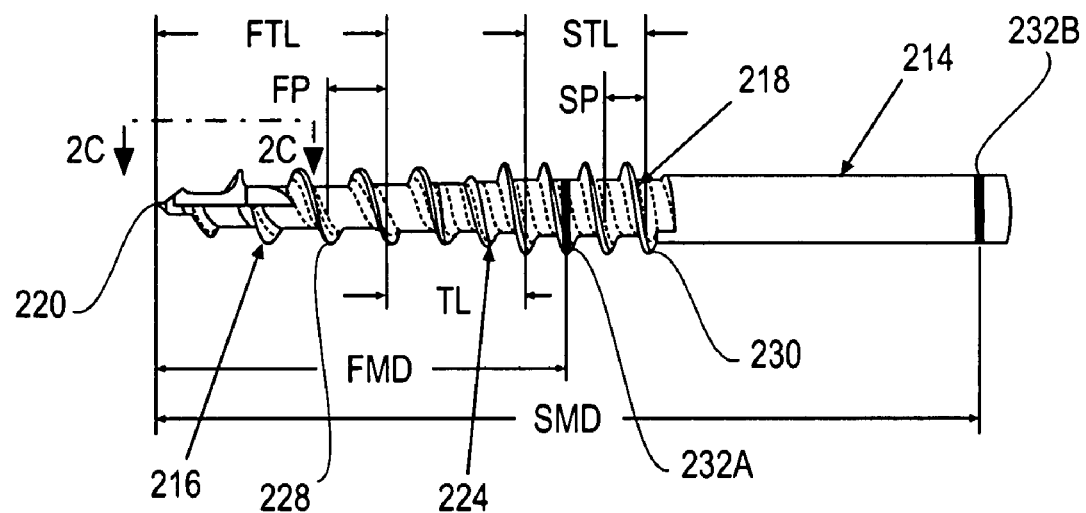
FIG. 2B is an enlarged detail view taken from FIG. 2A.

FIG. 2B is an enlarged detail view of a portion of the pin body 214 near the distal end 220 including the first threaded region 216, the second threaded region 218, and the transition region 224 positioned between the threaded regions 216, 218. As mentioned above, the first threaded region 216 and the second threaded region 218 are uniquely designed so that the bone regions 12A, 12B (illustrated in FIG. 1) are aggressively compressed together during insertion of the compression pin 210.

The design, shape, and size of the regions 216, 216, 224 can be varied pursuant to the teachings provided herein to achieve compression between the bone regions 12A, 12B. In one embodiment, the first threaded region 216 has one or more first threads 228 having a first size and shape, and the second threaded region 218 has one or more second threads 230 having a second size and shape. In one embodiment, the first and second threads 228, 230 spiral around the perimeter of the pin body 214. Stated in another fashion, the first threads 228 form a continuous helical rib in the first threaded region 216, and the second threads 230 form a continuous helical rib in the second threaded region 218. Further, the transition region 224 separates the threaded regions 216, 218 and provides an area in which the first threads 228 taper down and the second threads 230 begin. Further, the transition region 224 can provide a small area without any threads.

The size of each region 216, 218, 224 can vary according to the desired bone usage for the compression pin 210. In one non-exclusive embodiment, the first threaded region 216 has a first threaded length "FTL" that is between approximately 0.2 inches and 0.6 inches; the transition region 224 has a transition length "TL" that is between approximately 0.1 inches and 0.3 inches; and the second threaded region 218 has a second threaded length "STL" that is between approximately 0.1 inches and 0.3 inches. Stated in another fashion, the first threaded region 216 includes between approximately 2 and 5 first threads 228, and the second threaded region 218 includes between approximately 2 and 5 second threads 230. However, other thread numbers and lengths can be utilized. In FIG. 2B, the first threaded length FTL is approximately 0.22 inches and includes at least three full first threads 228; the transition length TL is 0.13 inches; and the second threaded length STL is approximately 0.12 inches and includes at least three full second threads 230.

Additionally, in one non-exclusive embodiment, the first threads 228 have a first thread pitch "FP" of between approximately 0.05 inches and 0.12 inches; and the second threads 230 have a second thread pitch "SP" of between approximately 0.03 inches and 0.08 inches. Although other thread pitches can be utilized. In FIG. 2A, the first thread pitch FP is approximately 0.0585 inches and the second thread pitch SP is approximately 0.0390 inches. Thus, the first thread pitch FP is different than the second thread pitch SP. In alternative, non-exclusive embodiments, the first thread pitch FP is at least approximately 10, 20, 50, 100, 120, 150, 180, 200 or 250 percent greater than the second thread pitch SP.

Moreover, the compression pin 210 can include one or more markers 232A, 232B that allows the doctor to easily determine how far the compression pin 210 is inserted in the bone regions 12A, 12B. The type, location and number of markers 232A, 232B can vary. In FIG. 2B, the compression pin 210 includes a first marker 232A that is a first marker distance "FMD" from the distal end 220, and a second marker 232B that is a second marker distance "SMD" from the distal end 220. For example, the first marker distance FMD can be approximately 0.39 inches and the second marker distance SMD can be approximately 0.79 inches. Further, each marker 232A, 232B can be a laser etched band that extends partly or completely around the circumference of the pin body 214.

Figure 2C:
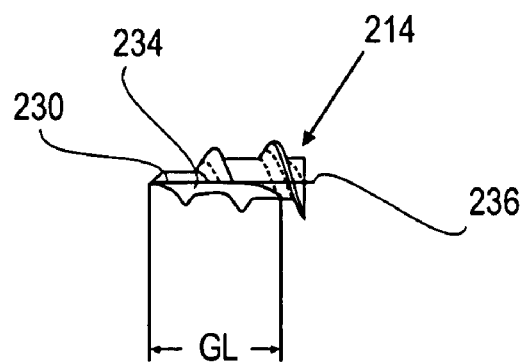
FIG. 2C is an enlarged detail view taken from FIG. 2B.

FIG. 2C is an enlarged detail view of the distal end 220 taken from FIG. 2B. FIG. 2C illustrates that the pin body 214 can include a distal groove 234 positioned near that distal end 220 that extends substantially parallel to a pin longitudinal axis 236. The distal groove 234 allows for a relatively sharp cutting distal end 220 that can facilitate insertion of the compression pin 210 into the bone regions 12A, 12B (Illustrated in FIG. 1). In FIG. 2C, the distal groove 234 has a groove length "GL" of approximately 0.13 inches. However, other groove lengths GL can be utilized. FIG. 2C also illustrates the relatively pointed distal end 220 and that in one embodiment the first thread 228 begins approximately 0.04 inches from the distal end 220.

Figure 2D:
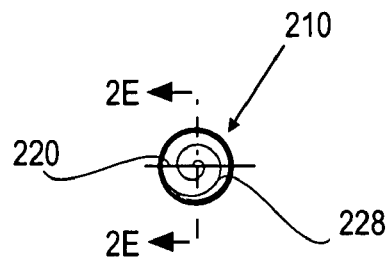
FIG. 2D is an end view of the compression pin of FIG. 2A.

FIG. 2D is an end view of the distal end 220 of the compression pin 210 and illustrates the helical nature of the first threads 228.

Figure 2E:
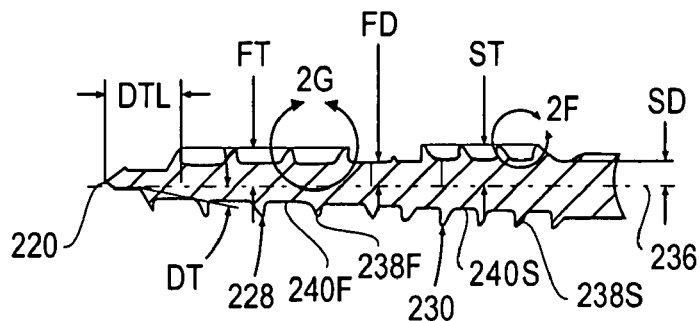
FIG. 2E is a cut-away view taken on line 2E-2E in FIG. 2D.

FIG. 2E is a cut-away view taken from FIG. 2D. FIG. 2E illustrates that the first threads 228 and the second threads 230 are tapered. More specifically, first threads 228 include first crests 238F and first roots 240F that are tapered relative to the longitudinal axis 236 with the taper increasing as the distance from the distal end 220 increases, and the second threads 230 includes second crests 238S and second roots 240S that are tapered relative to the longitudinal axis 236 with the taper increasing as the distance from the distal end 220 increases. The amount of taper of each of the threads 228, 230 can vary. For example, the first crests 238F of the first threads 228 can have a first taper "FT" of between approximately 1 and 2 degrees, and the second crests 238S of the second threads 230 can have a second taper "ST" of between approximately 1 and 2 degrees. In FIG. 2E, the first taper FT is approximately 1.25 degrees and the second taper ST is approximately 1.25 degrees. In this embodiment, the first taper FT is approximately equal to the second taper ST. Alternatively, for example, the first taper FT can be different that the second taper ST.

FIG. 2E also illustrates the first roots 240F of the first threads 228 have a first diameter "FD" near the proximal edge of the first threaded region 216 that is approximately 0.021 inches, and the second roots 240S of the second threads 230 have a second diameter "SD" near the proximal edge of the second threaded region 218 that is approximately 0.026 inches. However, other dimensions can be utilized.

Additionally, FIG. 2E illustrates that the distal end 220 can also be tapered. In FIG. 2E, for example, the distal end 220 can have a distal taper "DT" of approximately 10 degrees. Further, the distal taper DT can extend a distal taper length DTL that is approximately 0.08 inches. However, other tapers and lengths can be utilized.

Figure 2F:
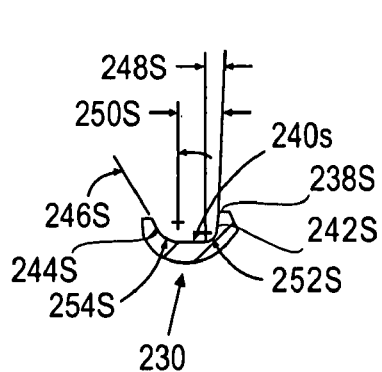
FIG. 2F is an enlarged detail view taken from FIG. 2E.

FIG. 2F is an enlarged detail view taken from FIG. 2E of one of the second threads 230. In this embodiment, the second thread 230 includes a ST leading surface 242S, a ST trailing surface 244S, the second crest 238S and the second root 240S. Further, (i) the ST trailing surface 244S is at a ST trailing angle 246S, (ii) the ST leading surface 242S is at a ST leading angle 248S, (iii) the second root 240S has a ST root width 250S, (iv) a junction between the ST leading surface 242S and the second root 240S is curved and has a second leading/root radius 252S, and (v) a junction between the ST trailing surface 244S and the second root 240S is curved and has a second trailing/root radius 254S.

Figure 2G:
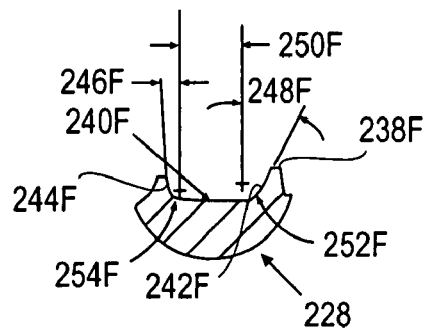
FIG. 2G is an enlarged detail view taken from FIG. 2E.

FIG. 2G is an enlarged detail view taken from FIG. 2E of one of the first threads 228. In this embodiment, the first thread 228 includes a FT leading surface 242F, a FT trailing surface 244F, the first crest 238F and the first root 240F. Further, (i) the FT trailing surface 244F is at a FT trailing angle 246F, (ii) the FT leading surface 242F is at a FT leading angle 248F, (iii) the first root 240F has a FT root width 250F, (iv) a junction between the FT leading surface 242F and the first root 240F is curved and has a first leading/root radius 252F, and (v) a junction between the FT trailing surface 244F and the first root 240F is curved and has a first trailing/root radius 254F.

It should be noted the thread angles 246F, 246S, 248F, 248S are measured relative to a reference line that is substantially perpendicular to the pin longitudinal axis 236 (illustrated in FIG. 2E).

Comparing FIGS. 2F and 2G, the first thread 228 has a different size and shape that is different that the size and shape of the second thread 230.

In one embodiment, the FT leading angle 248F is different than the ST leading angle 248S. In alternative, non-exclusive embodiments, the FT leading angle 248F is at least approximately 2, 5, 10, 20, 25, 28, or 30 degrees different and greater than the ST leading angle 248S. For example, the FT leading angle 248F can be approximately thirty degrees and the ST leading angle 248S can be approximately two degrees.

Additionally, the FT trailing angle 246F is different than the ST trailing angle 246S. In alternative, non-exclusive embodiments, the FT trailing angle 246F is at least approximately 2, 5, 10, 20, 25, 28, or 30 degrees different and less than the ST trailing angle 246S. For example, the FT trailing angle 246F can be approximately two degrees and the ST trailing angle 246S can be approximately thirty degrees.

Moreover, the FT root width 250F can be different than the ST root width 250S. In alternative, non-exclusive embodiments, the FT root width 250F is at least approximately 2, 5, 10, 20, 50, 100, 120, 150, 180, 200, 250, or 300 percent different and greater than the ST root width 250S. Stated in another fashion, in alternative, non-exclusive embodiments, the FT root width 250F is at least approximately 1.2, 1.5, 1.8, or 2 times greater than the ST root width 250S. For example, the FT root width 250F can be approximately 0.033 inches and the ST root width 250S can be approximately 0.014 inches.

Additionally, the second leading/root radius 252S is different than the first leading/root radius 252F. In alternative, non-exclusive embodiments, the first leading/root radius 252F is at least approximately 2, 5, 10, 20, 50, 100, 150, 200, 250, or 300 percent different and greater than the second leading/root radius 252S. For example, the first leading/root radius 252F can be approximately 0.012 inches and the second leading/root radius 252S can be approximately 0.006 inches.

Moreover, the second trailing/root radius 254S is different than the first trailing/root radius 254F. In alternative, non-exclusive embodiments, the first trailing/root radius 254F is at least approximately 2, 5, 10, 20, 50, 100, 150, 200, 250, or 300 percent different and less than the second trailing/root radius 254S. For example, the first trailing/root radius 254F can be approximately 0.006 inches and the second trailing/root radius 254S can be approximately 0.012 inches.

It should also be noted that the first thread 228 has a first thread cross-sectional shape and the second thread 230 has a second thread cross-sectional shape. In one embodiment, the first thread cross-sectional shape is substantially opposite to the second thread cross-sectional shape. Stated in another fashion, in certain embodiments, the first thread cross-sectional shape is an approximate mirror image to the second thread cross-sectional shape. With this design, in certain embodiments, during insertion of the compression pin 210, the first threaded region 216 and the second threaded region 218 cooperate to aggressively compress the bone regions 12A, 12B together.

Stated in another fashion, the cross-section of first tooth 228 between the FT leading surface 242F, the first crest 238F and the FT trailing surface 244F cooperate to form a truncated, generally right first triangle. Similarly, the cross-section of second tooth 230 between the ST leading surface 242S, the second crest 238S and the ST trailing surface 244S cooperate to form a truncated, generally right second triangle. Further, the first triangle and the second triangle are substantially similar but mirror images of each other.

It should also be noted that in one embodiment, (i) the FT leading angle 248F is approximately equal to the ST trailing angle 246S, (ii) the FT trailing angle 246F is approximately equal to the ST leading angle 248S, (iii) the first leading/root radius 252F is approximately equal to the second trailing/root radius 254S, and (iv) the first trailing/root radius 254F is approximately equal to the second leading/root radius 252S.

Figure 3A:
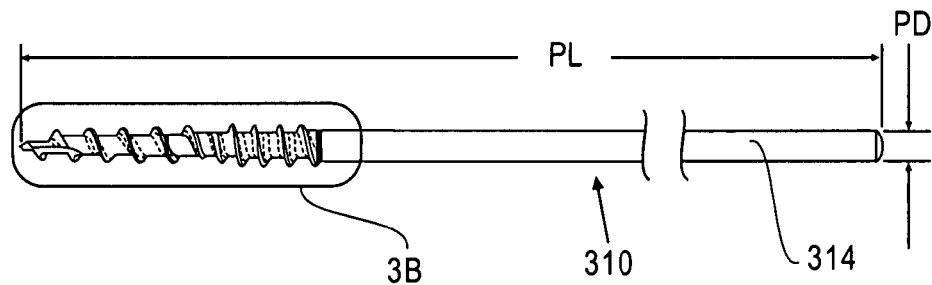
FIG. 3A is a side view of a second embodiment of a compression pin having features of the present invention.

FIG. 3A is a side view of another embodiment of a compression pin 310 that is somewhat similar to the compression pin 210 illustrated in FIGS. 2A-2G and described above. In this embodiment, the pin body 314 has a pin diameter (PD) of approximately 0.062 inches and a pin length (PL) of approximately 3.4 inches.

Figure 3B:
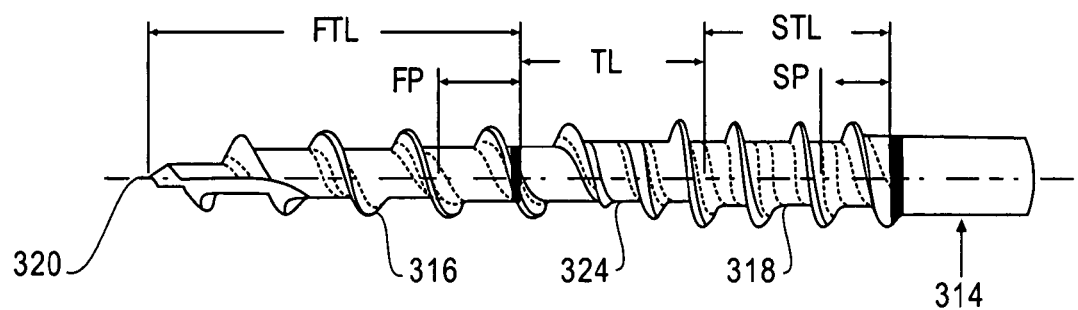
FIG. 3B is an enlarged detail view taken from FIG. 3A.

FIG. 3B is an enlarged detail view of a portion of the pin body 314 near the distal end 320 including the first threaded region 316, the second threaded region 318, and the transition region 324. In this embodiment, the first threaded length "FTL" is approximately 0.40 inches, the second threaded length "STL" is approximately 0.18 inches, and the transition length TL is approximately 0.20. Further, the first thread pitch FP is approximately 0.09 inches, and the second thread pitch SP is approximately 0.06 inches.

Figure 3C:
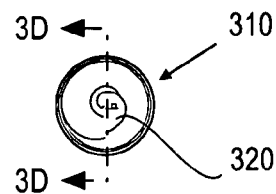
FIG. 3C is an end view of the compression pin of FIG. 3A.

FIG. 3C is an end view of the distal end 320 of the compression pin 310.

Figure 3D:
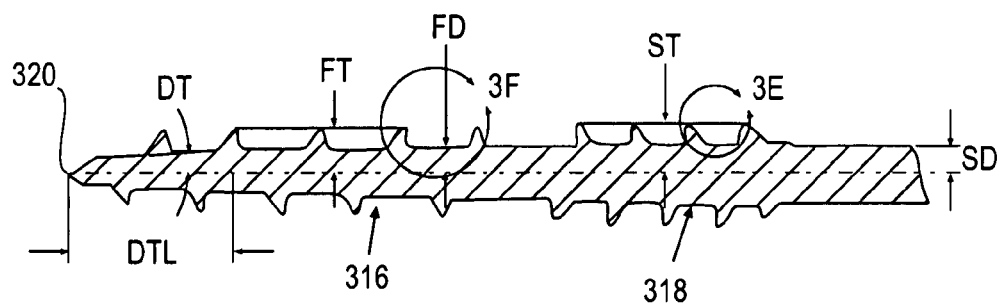
FIG. 3D is a cut-away view taken on line 3D-3D in FIG. 3C.

FIG. 3D is a cut-away view taken from FIG. 3C. In this embodiment, (i) the first taper FT is approximately 1 degree, (ii) the second taper "ST" is approximately 1 degree, (iii) the first threaded region 316 has a first diameter FD near the proximal edge of the first threaded region 316 that is approximately 0.028 inches, (iv) the second threaded region 318 has a second diameter SD near the proximal edge of the second threaded region 318 that is approximately 0.033 inches, (v) the distal end 320 has a distal taper DT of approximately 5 degrees that extends a distal taper length DTL of approximately 0.183 inches.

Figure 3E:
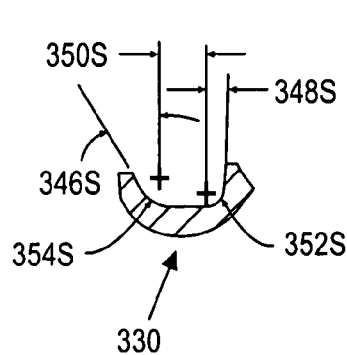
FIG. 3E is an enlarged detail view taken from FIG. 3D.

FIG. 3E is an enlarged detail view taken from FIG. 3D of one of the second threads 330. In this embodiment, the ST trailing angle 346S, the ST leading angle 348S, the second leading/root radius 352S, and the second trailing/root radius 354S are similar to the corresponding values detailed above. However, in this embodiment, the ST root width 350S is approximately 0.03 inches.

Figure 3F:
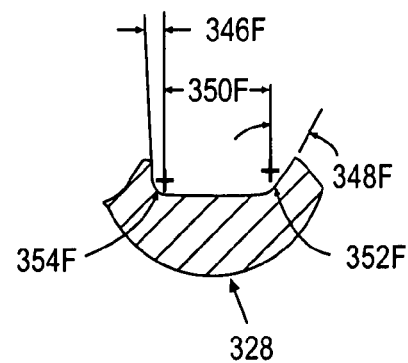
FIG. 3F is an enlarged detail view taken from FIG. 3D.

FIG. 3F is an enlarged detail view taken from FIG. 3D of one of the first threads 328. In this embodiment, the FT trailing angle 346F, the FT leading angle 348F, the first leading/root radius 352F, and the first trailing/root radius 354F are similar to the corresponding values detailed above. However, in this embodiment, the FT root width 350F is approximately 0.059 inches.

Figure 4A:
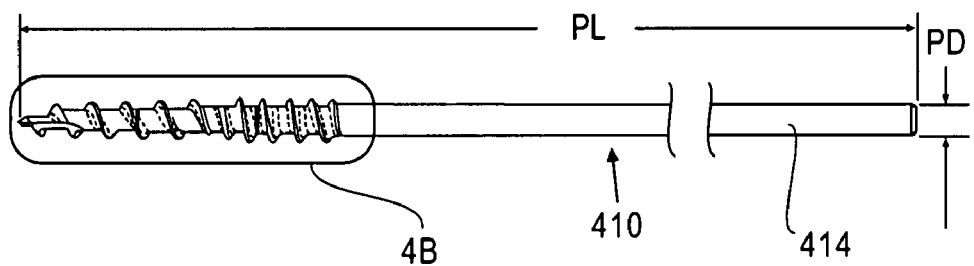
FIG. 4A is a side view of a third embodiment of a compression pin having features of the present invention.

FIG. 4A is a side view of another embodiment of a compression pin 410 that is somewhat similar to the compression pin 210 illustrated in FIGS. 2A-2G and described above. In this embodiment, the pin body 414 has a pin diameter (PD) of approximately 0.071 inches and a pin length (PL) of approximately 3.65 inches.

Figure 4B:
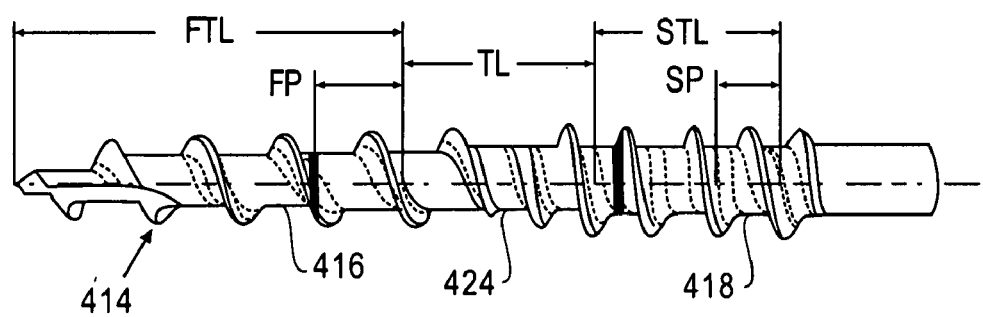
FIG. 4B is an enlarged detail view taken from FIG. 4A.

FIG. 4B is an enlarged detail view of a portion of the pin body 414 near the distal end 420 including the first threaded region 416, the second threaded region 418, and the transition region 424. In this embodiment, the first threaded length "FTL" is approximately 0.51 inches, the second threaded length "STL" is approximately 0.23 inches, and the transition length TL is approximately 0.25 inches. Further, the first thread pitch FP is approximately 0.1125 inches, and the second thread pitch SP is approximately 0.0750 inches.

Figure 4C:
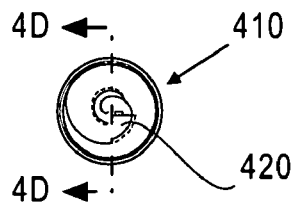
FIG. 4C is an end view of the compression pin of FIG. 4A.

FIG. 4C is an end view of the distal end 420 of the compression pin 410.

Figure 4D:
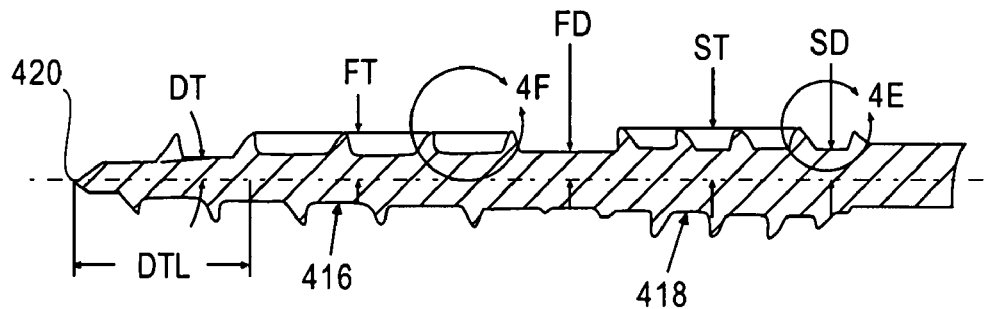
FIG. 4D is a cut-away view taken on line 4D-4D in FIG. 4C.

FIG. 4D is a cut-away view taken from FIG. 4C. In this embodiment, (i) the first taper FT is approximately 1 degree, (ii) the second taper "ST" is approximately 1 degree, (iii) the first threaded region 416 has a first diameter FD near the proximal edge of the first threaded region 416 that is approximately 0.038 inches, (iv) the second threaded region 418 has a second diameter SD near the proximal edge of the second threaded region 418 that is approximately 0.045 inches, (v) the distal end 320 has a distal taper DT of approximately 5 degrees that extends a distal taper length DTL of approximately 0.229 inches.

Figure 4E:
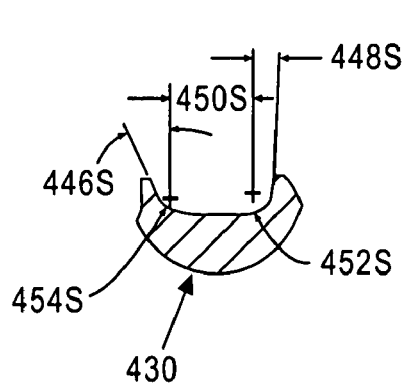
FIG. 4E is an enlarged detail view taken from FIG. 4D.

FIG. 4E is an enlarged detail view taken from FIG. 4D of one of the second threads 430. In this embodiment, the ST trailing angle 446S, the ST leading angle 448S, the second leading/root radius 452S, and the second trailing/root radius 454S are similar to the corresponding values detailed above. However, in this embodiment, the ST root width 450S is approximately 0.04 inches.

Figure 4F:
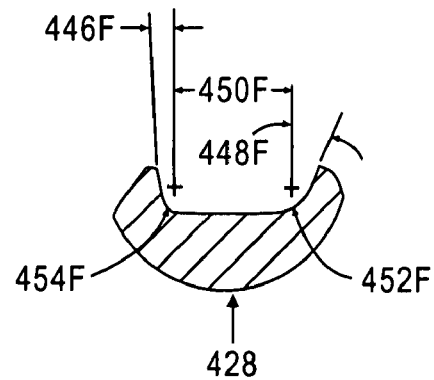
FIG. 4F is an enlarged detail view taken from FIG. 4D.

FIG. 4F is an enlarged detail view taken from FIG. 4D of one of the first threads 428. In this embodiment, the FT trailing angle 446F, the FT leading angle 448F, the first leading/root radius 452F, and the first trailing/root radius 454F are similar to the corresponding values detailed above. However, in this embodiment, the FT root width 450F is approximately 0.078 inches.

While the particular compression pin 10 as shown and disclosed herein is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A compression pin for urging two bone regions together, the compression pin comprising:
a pin body having a distal end, an opposed proximal end, a first threaded region positioned near the distal end, and a second threaded region positioned near the first threaded region,
the first threaded region including a first thread extending from a first diameter, the first thread having a first leading surface that is at a first leading angle and having a first radius of curvature formed between the first leading surface and the first diameter, and
the second threaded region including a second thread extending from a second diameter, the second thread having a second leading surface that is at a second leading angle that is at least two degrees different than the first leading angle, the second thread having a second radius of curvature formed between the second leading surface and the second diameter, wherein the second radius of curvature is at least two percent smaller than the first radius of curvature.

2. The compression pin of claim 1 wherein the second leading angle is at least ten degrees different than the first leading angle.

3. The compression pin of claim 1 wherein the second leading angle is at least twenty degrees different than the first leading angle.

4. The compression pin of claim 1 wherein ST leading angle is at least twenty-five degrees different than the first leading angle.

5. The compression pin of claim 1 wherein the second leading angle is approximately two degrees and the first leading angle is approximately thirty degrees.

6. The compression pin of claim 1 wherein the first thread has a first trailing surface that is at a first trailing angle, and the second thread has a second trailing surface that is at a second trailing angle that is at least two degrees different than the first trailing angle.

7. The compression pin of claim 6 wherein the second trailing angle is at least ten degrees different than the first trailing angle.

8. The compression pin of claim 6 wherein the second trailing angle is at least twenty degrees different than the first trailing angle.

9. The compression pin of claim 6 wherein the second trailing angle is at least twenty-eight degrees different than the first trailing angle.

10. The compression pin of claim 6 wherein the second trailing angle is approximately thirty degrees and the first trailing angle is approximately two degrees.

11. The compression pin of claim 1 wherein the first thread has a first root width, and the second thread has a second root width that is at least two percent different than the first root width.

12. The compression pin of claim 1 wherein the first thread has a first root width, and the second thread has a second root width that is at least two percent different than the first root width.

13. The compression pin of claim 1 wherein the first thread has a first thread cross-sectional shape and the second thread has a second thread cross-sectional shape and wherein the first thread cross-sectional shape is approximately opposite to the second thread cross-sectional shape.

14. A compression pin for urging two bone regions together, the compression pin comprising:
    a pin body having a distal end, an opposed proximal end, a first threaded region positioned near the distal end, and a second threaded region positioned near the first threaded region,
    the first threaded region including a first thread extending from a first diameter, the first thread having a first trailing surface that is at a first trailing angle and a first radius of curvature formed between the first trailing surface and the first diameter, and
    the second threaded region including a second thread extending from a second diameter, the second thread having a second trailing surface that is at a second trailing angle that is at least two degrees different than the first trailing angle, the second thread having a second radius of curvature formed between the second trailing surface and the second diameter, wherein the second radius of curvature is at least two percent greater than the first radius of curvature.

15. The compression pin of claim 14 wherein the second trailing angle is at least ten degrees different than the first trailing angle.

16. The compression pin of claim 14 wherein the second trailing angle is at least twenty degrees different than the first trailing angle.

17. The compression pin of claim 14 wherein the second trailing angle is at least twenty-eight degrees different than the first trailing angle.

18. The compression pin of claim 14 wherein the second trailing angle is approximately thirty degrees and the first trailing angle is approximately two degrees.

19. The compression pin of claim 14 wherein the first thread has a first thread cross-sectional shape and the second thread has a second thread cross-sectional shape and wherein the first thread cross-sectional shape is approximately opposite to the second thread cross-sectional shape.

20. A compression pin for urging two bone regions together, the compression pin comprising:
    a pin body having a distal end, an opposed proximal end, a first threaded region positioned near the distal end, and a second threaded region positioned near the first threaded region, the first threaded region including a first thread extending from a first diameter and having a first leading surface and a first thread cross-sectional shape, and the second threaded region including a second thread extending from a second diameter and having a second leading surface and a second thread cross-sectional shape that is approximately opposite to the first thread cross-sectional shape,
    wherein a first radius formed between the first diameter and the first leading surface is at least twenty percent greater than a second radius formed between the second diameter and the second leading surface.

21. The compression pin of claim 20 wherein the first leading surface is at a first leading angle, and the second leading surface is at a second leading angle that is at least two degrees different than the first leading angle.

22. The compression pin of claim 21 wherein the first thread has a first trailing surface that is at a first trailing angle, and the second thread has a second trailing surface that is at a second trailing angle that is at least two degrees different than the first trailing angle.

* * * * *